United States Patent

Abouaf et al.

[11] Patent Number: 5,871,547
[45] Date of Patent: Feb. 16, 1999

[54] HIP JOINT PROSTHESIS HAVING A ZIRCONIA HEAD AND A CERAMIC CUP

[75] Inventors: Marc Abouaf, Westboro; Edward Lilley, Shrewsbury, both of Mass.; Daniel Urffer, Morieres; Bernard Cales, Evreux, both of France; Oh-Hun Kwon, Westboro, Mass.; Yves Stefani, Vanves, France

[73] Assignee: Saint-Gobain/Norton Industrial Ceramics Corp., Worcester, Mass.

[21] Appl. No.: 698,635

[22] Filed: Aug. 16, 1996

Related U.S. Application Data

[63] Continuation-in-part of Ser. No. 609,711, Mar. 1, 1996, abandoned.
[51] Int. Cl.$^6$ ........................................................ A61F 2/32
[52] U.S. Cl. .............................................. 623/22; 623/18
[58] Field of Search .................................. 623/18, 19, 20, 623/22, 23

[56] References Cited

U.S. PATENT DOCUMENTS

| | | | |
|---|---|---|---|
| 3,744,061 | 7/1973 | Frost | 3/1 |
| 4,198,711 | 4/1980 | Zeibig | 623/23 |
| 4,636,218 | 1/1987 | Fukuura et al. | 623/18 |
| 5,338,771 | 8/1994 | Neumann et al. | |

FOREIGN PATENT DOCUMENTS

| | | |
|---|---|---|
| 248117A2 | 12/1987 | European Pat. Off. . |
| 410711A1 | 1/1991 | European Pat. Off. . |
| 437390A1 | 7/1991 | European Pat. Off. . |
| 453694A1 | 10/1991 | European Pat. Off. . |
| 573694A2 | 12/1993 | European Pat. Off. . |
| 590241A1 | 4/1994 | European Pat. Off. . |
| 608997A1 | 8/1994 | European Pat. Off. . |
| 2417972 | 9/1979 | France . |
| 2628314 | 9/1989 | France . |
| 1371335 | 10/1974 | United Kingdom . |

OTHER PUBLICATIONS

Willmann, G. et al., *Wear Characteristics of Sliding Pairs of Zirconia (Y–TZP) for Hip Endoprostheses,* Biomaterials 1996, vol. 17 No. 22, pp. 2157–2162.
Ravaglioli et al, "Bioceramics", Title Page and pp. 160 and 197.
A. Zeibig and H. Luber, "Bioceramic Hip Joint Components—Industrial Production and Testing Procedures to Ensure High Functional Reliability", Ceramics in Surgery, 1983, Netherlands pp. 267–275.
G. W. Stachowiak and G. B. Stachowiak, "Unlubricated Friction And Wear Behaviour of Toughned Zirconia Ceramics", Wear, 132 (1989) pp. 151–171.
O. O. Ajayi and K. C. Ludema, "Surface Damage Of Structural Ceramics Implications For Wear Modeling" Wear, 124 (1988) pp. 237–257.
H. G. Scott, "Friction And Wear Of Zirconia At Very Low Sliding Speeds", Advanced materials Laboratory, CSIRO Division of Materials Science, Melbourne, Victoria, Australia, pp. 8–12.
H. Liang and T. E. Fischer, "Effect of Grain Boundary Impurities on the Mechanical and Tribological Properties of Zirconia Surfaces", J. Am. Ceramic. Soc. 76(2) 1993, pp. 325–329.

(List continued on next page.)

*Primary Examiner*—Michael J. Milano
*Attorney, Agent, or Firm*—Thomas M. DiMauro

[57] ABSTRACT

This invention relates to a biojoint prosthesis comprising:
  a) a prosthetic comprising a first component having an outer surface comprising at least 90 mol% zirconia, and
  b) a second component having a surface shaped to receive the outer surface of the first component,
wherein the outer surface of the first component is received on the surface of the second component, and
wherein a) at least a portion of the surface of the second component receiving the first component comprises a ceramic having a surface roughness of no more than 100 nm, and b) the outer surface of the first component has a surface roughness of no more than 100 nm.

36 Claims, 3 Drawing Sheets

OTHER PUBLICATIONS

T. E. Fischer, M. P. Anderson, S. Jahanmir and R. Salher, "Friction And Wear Of Tough And Brittle Zirconia In Nitrogen, Air, Water, Hexadecane And Hexadecane Containing Stearic Acid", Wear, 124 (1988) pp. 133–148.

K. E. Amin and D. Nag, Tribological Characteristics Of Zirconia–Yttria Ceramics, American Ceranic Society Bulletin, Vo. 74, N. 5, May 1995, pp. 80–84.

S. M. Hsu, V. S. Nagarajan and H. Liu, "Advanced Ceramics For Structural And Tribological Applications", 34th Annual Conference Of Metallurgists Of CIM, Vancouver, British Columbia, Aug. 20–24, 1995 pp. 6–21.

G. Willmann, H. J. Früh and H. G. Pfaff, "Wear Characteristics Of Slifing Pairs Of Zirconia (Y–TZP) For Hip Endoprstheses", Biomaterials, vol. 17, No. 22 (1996), Great Britain, pp. 2157–2162.

HIP JOINT PROSTHESIS HAVING A ZIRCONIA HEAD AND A CERAMIC CUP

This application is a continuation-in-part of application Ser. No. 08/609,711 filed on Mar. 1, 1996, now abandoned.

BACKGROUND OF THE INVENTION

In surgeries requiring a total hip joint replacement, both the acetabulum and the upper portion of the femur must be replaced, and appropriate materials must be selected as the replacement components. During the 1970's, the femoral prosthetic component was typically made of a metal such as stainless steel, alloys of Cr—Co—Mo and titanium, while the mating acetabular cup was typically made of ultra high molecular weight polyethylene (UHMWPE). However, it soon became apparent that the metal-UHMWPE coupling produced significant amounts of polyethylene wear debris in vivo. This debris has been heavily implicated in the osteolytic destruction of periarticular tissues and the subsequent loosening of the hip joint prosthesis. Consequently, the medical community began to consider replacement materials for the metal heads.

Because of the wear and debris problem, standardized testing methods were also developed to help compare the wear rates of candidate materials for hip joint prosthesis components. Determining the wear-related suitability of components for use in a hip joint prosthesis typically involves performing a standard pin-on-disc wear test, such as ASTM F 732 82, and characterizing its results by a normalized wear factor, k. The wear factor, k, is defined as the wear volume V (in $mm^3$) of a material, divided by the product of the load P (in N) and the sliding distance X (in m). According to Saikko, Wear 166 (1993) 169–178, a wear factor of $10^{-9}$ $mm^3/Nm$ is "extremely low" while a wear factor of $10^{-7}$ $mm^3/Nm$ is "considerable".

From these wear tests, alumina was identified as a candidate replacement material. The reported wear factors k of the UWPE\alumina couple of about $10^{-7}$ $mm^3/Nm$ to $10^{-9}$ $mm^3/Nm$ were found to be superior to the metal\HMWPE couple. Accordingly, modular femur components comprising an alumina head taper fit to a metal stem were developed, and these components were coupled with both UHMWPE and alumina cups. Although the alumina-UHMWPE and alumina-alumina couplings produce less wear debris, the low strength of alumina (only about 600 MPa) has hindered its widespread acceptance. Because of the unreliability associated with the low strength of alumina, other ceramic materials have been considered.

Over the past five years, artificial hip joint prostheses having zirconia heads have gained acceptance in the medical community. As the strength of partially stabilized zirconia is typically between about 900–1300 MPa and its toughness is at least about 5 MPa $m^{1/2}$, it is more reliable than alumina. In fact, the superior mechanical properties of zirconia has even enabled its use in small 22 mm heads. In all hip joint prostheses using zirconia heads, UHWPE cups have been used. See, for example, U.S. Pat. No. 5,181,929, assigned to Ceramiques Techniques Desmarquest; Willmann (of Cerasiv), Biomedizinische Technik 39(4) (1994) 73–78; Saikko, Wear 166 (1993) 169–178; Derbyshire, Med. Eng. Phys. 16 (1994) 229–236; Tateishi Mat. Sci. Eng. C1 (1994) 121–125; Japanese Patent Publication (Kokoku) 5-75423; Streicher (of Sulzer) "Bioceramics, Vol. 4", (1991) 9–16; and Schwartz (of Richards), "36th Ann. Mtg. ORS" 1990 483. Since the reported production of UHWPE debris has been extremely variable in this case (a wear factor k of $10^{-7}$ $mm^3/Nm$ according to Streicher and Derbyshire to $10^{-9}$ $mm^3/Nm$ according to Saikko), there remains a continuing need to identify materials for use in acetabulum cups which, when coupled with zirconia heads, produce even smaller amounts of debris than a UHMWPE cup.

Researchers studying the wear of zirconia-ceramic couplings have reported extremely high wear. For example, the results reported by Ludema, in "Advanced Ceramics for Structural and tribological Applications" (1995) 37–45, yield an alumina plate-zirconia pin total wear factor of about $10^{-5}$ $mm^3/Nm$, and a zirconia plate-alumina pin total wear factor of over $10^{-5}$ $mm^3/Nm$. The results reported by Medevielle et al., in J. Eur. Cer. Soc. 15 (12) (1995) 1193–1200, yield an alumina plate-zirconia pin total wear factor of about $10^{-6}$ $mm^3/Nm$ (assuming a test period of 30 minutes). Tucci, in Wear, 172, (1994) 111–119, reports yttria tetragonal polycrystal ("YTZP") zirconia plate-alumina pin wear factors ranging from $10^{-5}$ $mm^3/Nm$ to $10^{-3}$ $mm^3/Nm$. Lastly, the results of Sudanese, in Alumina vs Zirconium Oxide: A Comparative Wear Test, in "Bioceramics 1989", pp. 237–240, Oonishi H, Aoki M, Sawai L (eds), yield a wear factor for a zirconia ring-zirconia disc coupling which was over 5000 times worse than an alumina-alumina coupling.

Because of the high wear factors associated with zirconia-ceramic couplings, the hip joint prosthesis field has considered and specifically rejected a zirconia head-ceramic cup coupling. For example, in Clarke, Clin. Orthop. 282 (1992) 19–30, the author points to the relative inferiority of zirconia in wear tests and warns that "there may be a cause for concern given the potential to mix and match alumina ceramic cups with zirconia balls". In Willmann, supra, Table 3 specifically discourages using a zirconia head and an alumina cup and bases that conclusion upon clinical and technical studies. Sudanese, supra, concludes that ". . . zirconium oxide cannot be used for ceramic-ceramic coupling prosthesis, due to its low wear resistance. It may be the bioceramic material of choice to make ceramic heads in hip prosthesis with [polyethilene] sockets." Although Kyocera JP Patent Publication 4303443 discloses an alumina head coupled with a cup having either an alumina or zirconia mating surface, its reference to a zirconia cup is merely prophetic and it does not disclose a zirconia head with a cup having an alumina mating surface. Since the wear mechanisms for the head and cup are different (see e.g., Medevielle's discussion and Ludema's results when the couples are switched), Kyocera's silence with respect to the zirconia head-alumina cup combination is notable.

Accordingly, there exists a continuing need for an acetabulum cup for use with a zirconia head which produces a wear factor of less than $10^{-7}$ $mm^3/Nm$.

SUMMARY OF THE INVENTION

In accordance with the present invention, there is provided a joint prosthesis comprising:

a) a prosthetic comprising a first component having an outer surface comprising at least 90 mol % zirconia, and b) a second component having a surface shaped to receive the outer surface of the first component, wherein the outer surface of the first component is received on the surface of the second component, and wherein a) at least a portion of the surface of the second component receiving the first component comprises a ceramic having a surface roughness of no more than 100 nm (preferably, no more than 50 nm), and b) the outer surface of the first component has a surface roughness of no more than 100 nm (preferably, no more than 50 nm).

Preferably, the joint prosthesis is a hip joint prosthesis comprising:

a) a femoral prosthetic comprising a substantially spherical ceramic head having an outer surface comprising at least 90 mol % zirconia, and b) an acetabular cup having a socket surface shaped to rotatably receive the ceramic head, wherein the outer surface of the ceramic head is received in the socket surface of the acetabular cup, and wherein a) at least a portion of the socket surface receiving the head comprises a ceramic having a surface roughness Ra of no more than 100 nm (preferably, no more than 50 nm), and b) the outer surface of the head has a surface roughness of no more than 100 nm (preferably, no more than 50 nm).

Preferably, the portion of the socket surface comprising a ceramic comprises at least one oxide, more preferably it consists essentially of either a biomedical grade alumina having a surface roughness of no more than 20 nm or a zirconia partially stabilized with between 2 and 5 mol % rare earth oxide and having a surface roughness of no more than 20 nm.

Preferably, the ceramic head consists essentially of a zirconia partially stabilized with between 2 and 5 mol % rare earth oxide ("PSZ"), and preferably has a surface roughness Ra of no more than 15 nm, more preferably no more than 10 nm.

DETAILED DESCRIPTION OF THE PRESENT INVENTION

Figure 1:
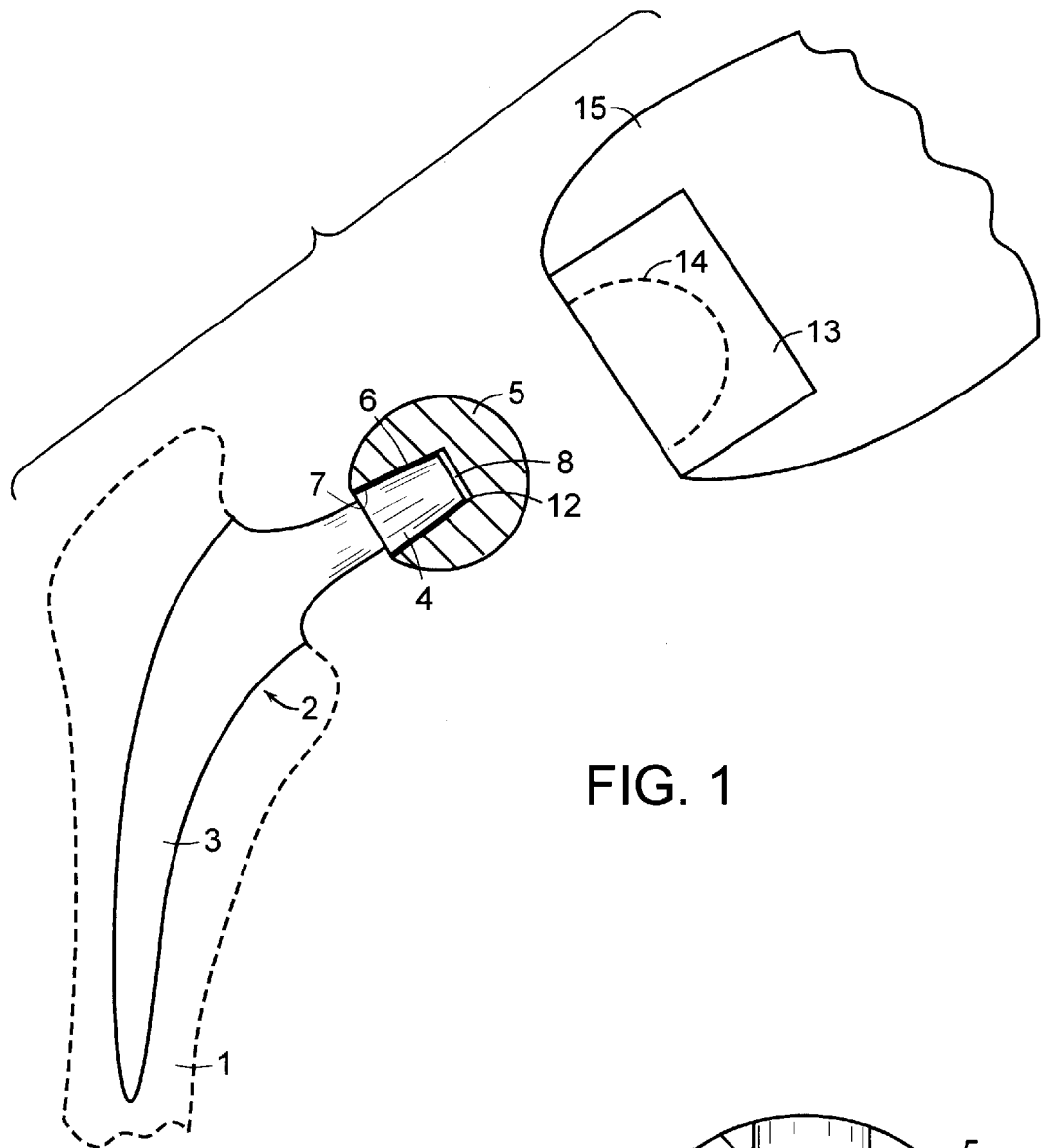
FIG. 1 shows a cross section of an embodiment of the present invention utilizing conventional hip joint prosthesis geometry.

It has been found that a pin-plate combination of hipped YTZP zirconia-hipped YTZP zirconia having surface roughnesses of about 11 nm and 8 nm, respectively, produced low wear rates in pin-on-discs wear tests designed for hip joint prosthesis applications. In particular, the wear factor k of the zirconia pin was found to be only 3–6×10$^{-8}$ mm$^3$/Nm. In a related test, an alumina ball having a surface roughness Ra of about 40 nm was slid against the same YTZP plate and a wear factor of 8.5×10$^{-9}$ mm$^3$/Nm was found for the ball and negligible wear was found for the YTZP plate. Concurrently, in an independent test, it has also been found that a YTZP-alumina couple produced lower wear rates than either YTZP—YTZP or alumina—alumina couples. Although the pin-on-disk test is only a screening test (and the zirconia head-alumina cup and zirconia head-zirconia cup couplings should still be validated on a joint simulator machine), the positive results indicate that ceramics in general, and smooth surfaced oxides such as alumina and zirconia in particular, are potential candidate materials for use with smooth zirconia surfaces in bioprosthetic joints such as hips, knees, toes, wrists, elbows, ankles and fingers in general, and in the acetabular cup of a hip joint prosthesis having a zirconia head in particular.

The present invention is surprising in light of the prior art teachings on ceramic wear. In general, the prior art taught that intrinsic factors such as toughness, hardness and thermal conductivity determine the initial wear, and that third body debris determines the wear rate thereafter. Without wishing to be tied to a theory, it is believed that the primary factor in producing the vastly superior wear factors k of the present invention is the heretofore unappreciated criticality of maintaining the surface roughness Ra of both of the articulating surfaces below 100 nm (preferably, beloww 50 nm) in order to achieve a wear factor of 10$^{-7}$ mm$^3$/Nm. The present invention relies on the belief that surface damage is less manageable than the art admits and that maintaining the surface roughness Ra at each surface below 100 nm can substantially prevent surface damage nucleation when the articulation is in the low force regime common to hip joint prosthesis articulating surfaces. Simply, it is believed that, in order to attain low wear rates in zirconia-ceramic hip joint prosthesis couples, the surfaces must be made smooth and kept smooth. In contrast, the prior art routinely controlled only one of the articulating surfaces' roughness, not both. For example, Medevielle et al. used as-sintered balls in their ball on ring tests. Ludema et al. not only reported just the surface roughness of their plates, they also used a low porosity alumina having a 217 nm. Tucci et al. reported that only the surface under tensile stress (i.e., the plate) was polished to a mirror finish and did not report the Ra of their low density alumina pins. Sudanese did not report the surface roughness for the zirconia ring.

The head component preferably consists essentially of a ceramic comprising at least about 90 mol % zirconia, and more preferably is a partially stabilized zirconia (PSZ). The PSZ is typically partially stabilized by a rare earth oxide at a concentration of between about 2 mol % and about 5 mol %. Most preferably, the PSZ is yttria stabilized tetragonal zirconia polycrystal (YTZP). Preferably, the YTZP has a mean grain size (SEM using ASTM E 112/82) of no more than 1 micron (um), preferably between 0.3 and 0.8 um. The bulk of the head should have a four point flexural strength of at least about 920 MPa, preferably at least 1300 MPa. Its density should be at least 99.7% of theoretical density, preferably at least 99.8%. In some embodiments, it has an elasticity modulus (ASTM C 674) of no more than 220 GPa; an open porosity of no more than 0.1%; less than 1% impurities; and a fracture toughness (as per Chantikul) of at least 5 MPa m$^{1/2}$.

Preferably, the head has an outer surface having a roughness of no more than 15 nm, more preferably no more than 10 nm. It has been found that controlling the surface roughness Ra of each surface to less than 15 nm reduces wear even more significantly. In one side-by-side comparison of YTZP pins having surface roughness Ra's of 11.5 nm and 25.6 nm, respectively, the wear rate of the smoother pins was found to be about seven times lower than the coarser pin. Generally, the outer surface of the head contains less than 10% monoclinic zirconia, preferably less than 5%. Most preferably, the outer surface consists essentially of 100% tetragonal zirconia.

Preferably, the outer surface of the head is made of the same material as the bulk of the head (i.e., the head is a monolith). However, it is contemplated that the outer layer of the head can be another material. In such a case, both the bulk and the outer surface preferably possesses mechanical characteristics similar to those disclose in U.S. Pat. No. 5,181,929, the specification of which is incorporated by reference.

In one preferred method of making the YTZP zirconia, the rare earth oxide powder and submicron zirconia powder are mixed, the mixture is cold isostatically pressed at between 50 and 400 MPa and appropriately green machined to form a green sphere which is then sintered at between about 1300° C. and 1500° C. for about 1 to 4 hours to achieve a density of at least 95%; and the sintered piece is hipped in an inert gas such as argon at between 1300° C. and 1500° C. for between 0.5 and 4 hours to produce a sintered sphere having a density of at least 99.9%, and a grain size of at most less than one micron. Without wishing to be tied to a theory, it is believed the hipping allows the densification to take place at a lower temperature, thus preventing substantial grain coarsening. It is also believed the hipping closes porosity and heals cracks which can promote wear.

In preferred embodiments, both the socket surface and the outer surface of the head each have a surface roughness of no more than 20 nm, preferably less than 10 nm, more preferably no more than 5 nm. In some embodiments, the outer surface of the ceramic head and the socket surface each have a surface roughness of no more than 15 nm. When a relatively hard material such as alumina is used as the socket surface, the preferred levels of roughness for the socket surface are smaller than those of the outer surface of the head because alumina is harder than zirconia and so is more apt to become a mini-grinding wheel and create a fracture in the zirconia surface. Therefore, in some embodiments in which the outer surface of the head is a PSZ and the socket surface consists essentially of alumina, the PSZ outer surface of the head has a surface roughness Ra of at least twice that of the alumina socket surface.

In some embodiments, the ceramic comprising at least a portion of the socket surface has a grain size of less than two microns, preferably less than one micron (by linear intercept method). Preferably, this ceramic has a density of at least 3.9 g/cc, more preferably at least 3.97 g/cc; and a grain size of between 0.4 and 0.9 um. In some embodiments, it has a 4 point flexural strength of at least 400 MPa, more preferably at least 550 MPa. In some embodiments, the socket surface comprises a ceramic comprising at least one oxide, preferably selected from the group consisting of alumina having a grain size of less than one micron, YTZP zirconia having a surface roughness Ra of no more than 15 nm, and zirconia-toughened alumina. Most preferably, the ceramic comprising at least a portion of the socket surface consists essentially of alumina.

A preferred alumina can be produced by sintering Ceralox APA-0.5 MgO alumina, available from Ceralox Corp. of Tuscon, Ariz., at about 1400 C. for about 60 minutes and then hipping at 1350 C. and 200 MPa for 45 minutes. In addition, sol gel processes such as those disclosed in U.S. Ser. No. 07/884,817, now abandoned, or U.S. Pat. No. 4,657,754, the specifications of which are incorporated by reference, can also be used to make fine grained alumina.

If zirconia toughened alumina is selected as the ceramic comprising at least a portion of the socket surface, then it is preferable to use a material comprising at least 20 vol % zirconia as disclosed in U.S. Pat. No. 4,316,964, the specification of which is incorporated by reference.

In one especially preferred embodiment, the head consists essentially of a YTZP zirconia, stabilized by between about 2 and 5 mol % rare earth oxide, having a flexural strength of at least 900 MPa, and preferably 1200 MPa, and surface roughness of no more than 10 nm, and a density of at least 99.7% of theoretical density; and the socket surface consists essentially of alumina having a flexural strength of at least 500 MPa, a surface roughness of no more than 10 nm, and a density of at least 99.8% of theoretical density. Without wishing to be tied to a theory, it is believed that maintaining these surface roughnesses on these materials will provide a total wear factor of no more than about $10^{-7}$ mm$^3$/Nm in zirconia pin-alumina disk tests using otherwise standard ASTM G99 test conditions.

The surfaces of each of the articulating surfaces should be polished by carefully staged grinding, lapping and finishing steps which insure that subsurface damage is minimized in achieving the smooth surface. One preferred method of polishing includes the procedure using diamond grit shown below in Table I.

TABLE I

| Slice | Grit Size um | Wheel type | Speed rpm | Pressure psi | Duration min | Ra um |
|---|---|---|---|---|---|---|
| A | #320 | blank | | | | 0.110 |
| B | 40 | alumina | 100 | 20 | 4 | 0.130 |
| C | 30 | platen | 25 | 25 | 3 | 0.028 |
| D | 9 | platen | 125 | 25 | 2 | 0.020 |
| E | 3 | texmet | 200 | 30 | 1.2 | 0.012 |
| F | 1 | cloth | 300 | 45 | 1.2 | 0.008 |
| G | 0.25 | cloth | 400 | 60 | <1 | 0.005 |

Preferably, the geometry of the head is essentially a spherical ball having a diameter of between about 22 and 32 mm and a single frustoconical cavity whose total angle at its apex is about 6 degrees. Examples of some preferred cavity designs are found in U.S. Pat. Nos. 4,964,869 and 5,181,929, the specifications of which are incorporated by reference. The sphericity of the head should at least be comparable to a sphericity of less than 5 um for a 28 mm head, as measured by Mitutoyo apparatus (BHN 305).

In some embodiments, substantially all of the acetabular cup comprises the ceramic comprising at least one oxide. Accordingly, cup designs such as those described in U.S. Pat. Nos. 3,924,275 and 4,636,218, the specifications of which are incorporated by reference, may be used. However, in other embodiments, the socket surface of the acetabular cup comprising the ceramic comprising at least one oxide is metal backed. In these situations, designs such as those described in EPO Patent Publication A1 0,278,205, may be used.

During surgery, the head is fitted to the metal stem portion of the femoral prosthetic by friction fitting the head's cavity upon the cone of the stem. Referring now to FIG. 1, there is provided a femoral prosthesis according to the present invention. The first end 3 of metal femoral rod 2 is implanted into femur 1. The second end of the rod 2 is shaped to a truncated cone 4. The cavity of the zirconia head 5 having about the same tape angle as cone 4 is press fitted onto cone 4. Side wall 6 of the head 5 defined by the frustoconical cavity is in contact over its substantial length with the lateral wall 7 of the male cone 4. A space 8 between the top of the cone 4 and the top of the cavity is also shown, thereby forming corners 12. Concurrently, the acetabular cup 13 having a socket surface 14 for receiving the head 5 is fitted into the pelvic bone 15. Lastly, the head 5 is positioned in the socket surface 14 of the acetabular cup 13 to form the hip joint.

Figure 2:
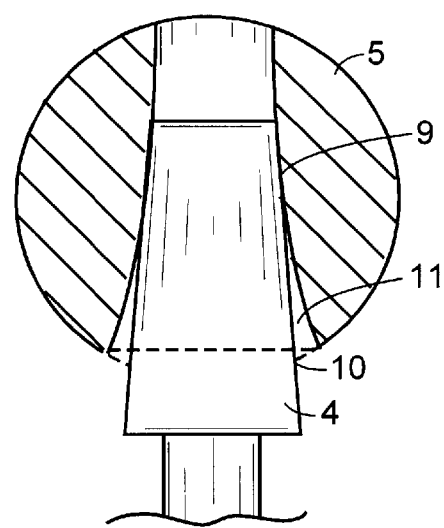
FIG. 2 shows a cross section of an embodiment of the present invention wherein the frustoconical cavity of the zirconia head completely traverses the head.
Figure 3:
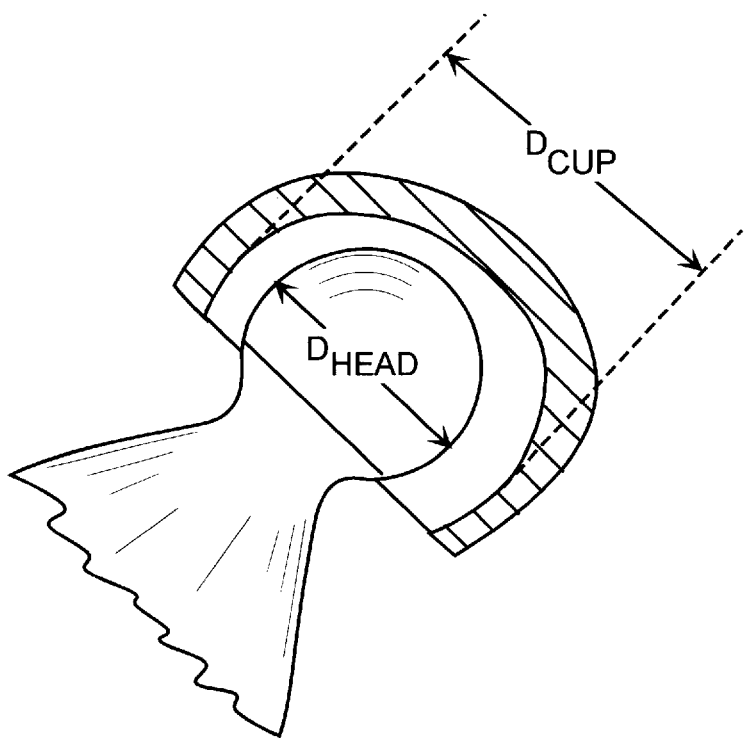
FIG. 3 shows a cross section of a head-cup combination in which the diameter of the cup is at least about 10% larger than the diameter of the head, thereby allowing rolling contact.

In some embodiments of the present invention, the head's frustoconical cavity extends fully through the head. See FIG. 2. It has been found that designing the cavity to completely traverse the head provides the head with a very high rupture strength. It is believed that the deep corners 12 of the cavities in conventional heads are regions of tensile stress concentration and that eliminating the corners eliminates this stress, thereby providing a more uniform hoop stress distribution along the sidewall 6.

In other embodiments, the cavity geometry includes a chamfer 11 which narrows inwardly from the surface of the head which intersects the metal cone. See FIG. 2. It has been found that providing this chamfer reduces the stress at the edge of the head.

Preferably, the metal femoral rod is a titanium alloy, Cr—Co—Mo, or any other metals or alloys used for making orthopedic implants.

When articulation occurs between the zirconia head and the ceramic socket surface, the sphericity mismatch results in point contact therebetween with stresses as high as 500 MPa. Because the ceramic socket is routinely designed to be hemispherical and just slightly larger than the head, the only relative movement is sliding movement and at least one of the contacting surfaces remains in contact with the opposing surface, thereby sustaining the high stress on that point. However, designing a cup to allow more freedom of movement for the head will create the rolling contact needed to allow different points to contact and relieve those particularly stressed initial points of contact. Therefore, in accordance with the present invention, there is also provided a hip joint prosthesis comprising:

a) a femoral prosthetic comprising a substantially spherical ceramic head having a diameter, and b) an acetabular cup having a socket surface shaped to rotatably receive the ceramic head, the socket surface having a diameter, wherein the ceramic head is received in the socket surface of the acetabular cup, and wherein the improvement comprises the diameter of the socket surface is larger, and preferably at least about 10% larger, than the diameter of the head, thereby providing rolling contact between the head and the socket surface. It is believed this design will also assist in expelling debris from the articulation interface.

Also in accordance with the present invention, there is provided a method of maintaining a low wear condition, comprising the step of:

a) sliding a first ceramic surface having a surface roughness of no more than 100 nm (preferably, no more than 50 nm) against a second ceramic surface having a surface roughness of no more than 100 nm (preferably, no more than 50 nm) with a force of between 5N and 25N, thereby providing a wear factor of no more than $10^{-8}$ mm$^3$/Nm.

Figure 4:
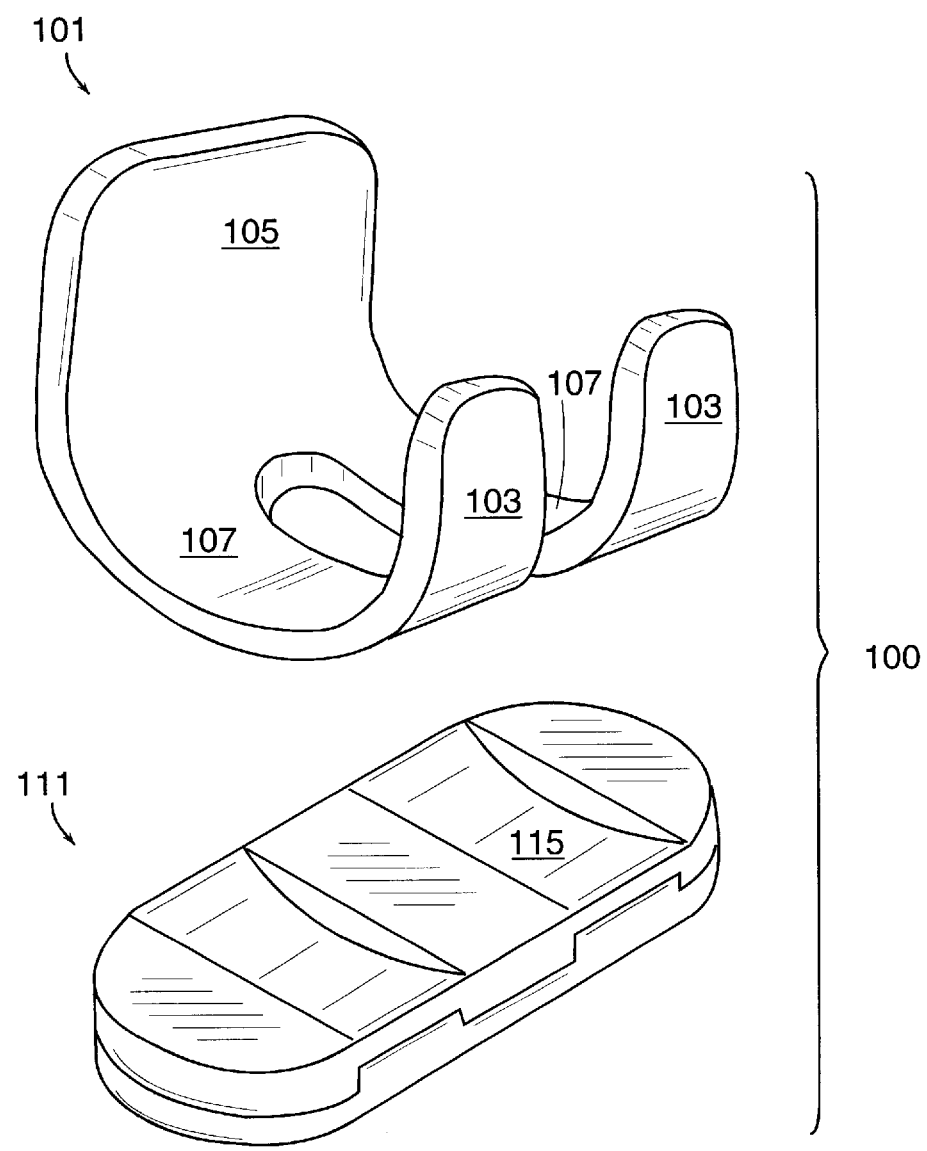
FIG. 4 is a drawing of a knee prosthesis of the present invention.

Moreover, it is believed that the criticality of controlling surface roughness Ra of both ceramic surfaces is also applicable to knee joint prostheses having zirconia femoral components. Therefore, in accordance with FIG. 4 and the present invention, there is also provided a knee joint prosthesis 100 comprising:

a) a femoral component 101 having a base 105 and a plurality of tynes 107 extending therefrom in the same direction, and b) a tibial plate 111 having a surface 115 shaped for receiving the tynes, wherein the tynes 107 have an outer surface 103 comprising zirconia partially stabilized by between 2 mol % and 5 mol % rare earth oxide and a surface roughness of no more than 100 nm (preferably, no more than 50 nm), and wherein the surface 115 of the tibial plate receiving the tynes 107 is a ceramic having a surface roughness of no more than 100 nm (preferably, no more than 50 nm).

The requirements set out above for the hip joint zirconia head and ceramic socket should also be considered to be applicable for the knee femoral zirconia femoral component and ceramic tibial plate surface.

EXAMPLE I

TZ-3Y, a hydrolyzed zirconia powder containing 3 mol % yttria was formed into tiles by uniaxial pressing at 20,000 lbs followed by cold isostatic pressing at 30,000 Kip. TZ-3Y was also formed into cylinders for making balls by pressing at 30,000 Kip. Both the tiles and cylinders were sintered in air at 1325 degrees C. for 2 hours and then hipped in argon at 1350 degrees C. for 1 hour. The final density of each was at least 99% of theoretical density.

The tiles were finished to about 8 nm using 1–15 um diamond paste on a Ectomet 4 Semi-Automatic polisher/grinder, available from Buehler of Tuscon, Ariz. The cylinders were machined into balls and then polished to a surface roughness Ra of about 11–12 nm by Chand Kare Technical Ceramics of Worcester, Mass.

Some of the balls were selected for heat treatment at 1450 degrees C. for 40 hours. The heat treatment caused pores in the balls of about 1 micron. Post-heat treatment cooling was performed rapidly to avoid LTD. Intrinsic properties of the heat treated balls (Balls 2 and 4) and the untreated balls (Balls 1 and 3) are shown in Table II.

TABLE II

|  | Balls 1 and 3 | Balls 2 and 4 |
| --- | --- | --- |
| Hardness | 12.8 GPa | 9.35 GPa |
| Toughness | 5.21 MPa m$^{1/2}$ | 7.24 MPa m$^{1/2}$ |
| Grain Size | 0.3 um | 0.87 um |

In addition, some of the heat treated balls and some of the untreated balls were repolished with 1 um diamond paste with a buffing wheel. The resulting surface roughnesses Ra are shown in Table III below.

Wear tests were performed on a Falex (TM) Multi-Specimen Wear Tester using ball on flat geometry. The flat was held stationary while the ball was rotated to create a circular scar on the flat. The tests were performed unlubricated in air at room temperature. A load of 9N was used. Velocity was 5 mm/sec. The total sliding distance was 40 meters. Wear volume was calculated via ASTM G99. The calculated wear factors are provided in Table III below.

TABLE III

| Ball | Heat Treatment | Repolish | Ra (nm) | Wear Factor |
| --- | --- | --- | --- | --- |
| 1 | NO | YES | 11.1 | $6 \times 10^{-8}$ mm$^3$/Nm |
| 2 | YES | YES | 11.5 | $6 \times 10^{-8}$ mm$^3$/Nm |
| 3 | NO | NO | 12.6 | $1.5 \times 10^{-7}$ mm$^3$/Nm |
| 4 | Yes | NO | 25.6 | $4 \times 10^{-7}$ mm$^3$/Nm |

As seen above, balls 1 and 2 have different hardnesses and toughnesses (intrinsic properties) but had the same surface roughness and same wear factor. Balls 1 and 3 have the same intrinsic properties, but the 10% smoother surface gave a three times lower wear factor. Balls 2 and 4 have the same intrinsic properties, but a 60% smoother surface gave a seven times lower wear rate. Accordingly, surface roughness Ra plays as large a role in the wear rates of zirconia-ceramic couples in this wear regime as hardness or toughness.

The experiments of Example I were performed without lubrication. Since lubrication often reduces the wear factor by a factor of about 5, and the actual hip joint prosthesis articulation may be lubricated by a fluid, controlling the surface roughness to a level below 25 nm for each YTZP surface may provide superior protection.

EXAMPLE II

A roller-plate was devised to study different combinations of ceramics in wear having relatively high surface roughnesses The selected ceramics included alumina, YTZP zirconia, zirconia toughened alumina (ZTA), and a sintered silicon nitride (SN). The YTZP was a PROZYR-type zirconia ceramic, a YTZP ceramic available from Ceramiques Techniques Desmarquest of Evreux, France. Each roller had an outer diameter of about 35 mm, a length of about 20 mm, and was believed to have a thickness of about 4 mm, and rotated at about 45 revolutions per minute against the plate. Each plate had a 20 mm×30 mm face and a 8 mm thickness, and moved back and forward against the roller in a 12 mm span at a speed of 1 mm/second. Total sliding distance was calculated by following a point on the face of the plate and was found to be about 2967 m. Roller and plate combinations were subject to wear testing at room temperature and 200N in Ringers solution for 24 hours with a normal force of 200N. The results are found in Table V below:

TABLE V

| Roller | Plate | Roller Ra (um) | Plate Ra (um) | Roller Weight Loss (%) | Plate Weight Loss (%) | Wear factor k | Friction Coeff't |
|---|---|---|---|---|---|---|---|
| Alumina | Alumina | 1.2 | 1.2 | 0.07 | 0.08 | $3.2 \times 10^{-5}$ | 0.22 |
| YTZP | ZTA | 0.9 | 0.16 | 0.30 | 0.58 | $1.9 \times 10^{-4}$ | 0.72 |
| YTZP | SN | 0.9 | 0.17 | 0.02 | 0.05 | $1.1 \times 10^{-4}$ | 0.69 |
| YTZP | YTZP | 0.9 | 0.17 | 2.4 | 2.1 | $1 \times 10^{-3}$ | 0.5 |
| YTZP | Alumina | 0.9 | 1.2 | 0.018 | neg. | $3.9 \times 10^{-6}$ | 0.25 |

The results indicate higher wear factors than those calculated in the other Examples. The reason for this difference is believed to be the difference in surface roughness Ra. In addition, the results showed the zirconia roller-alumina plate combination to be superior to the alumina roller-alumina plate combination, and far superior to the zirconia roller-zirconia plate combination.

EXAMPLE III

In this experiment, an alumina ball having a surface roughness of about 40 nm replaced the YTZP ball of Example I and the load was about 20N. The wear factor of the alumina ball was found to be about $8.5 \times 10^{-9}$ mm$^3$/NM, while the wear factor for the YTZP plate was negligible. Although it may have been more appropriate (for the purposes of evaluating a hip joint prosthesis having a zirconia head and a ceramic cup) to test an alumina plate and a YTZP ball, these results suggest the alumina in a zirconia-alumina couple need not be as smooth as the zirconia in a zirconia-zirconia couple in order to attain good results.

EXAMPLE IV

Alumina and zirconia ceramic specimens were used in wear testing experiments to screen these materials for possible use as prosthetic implant articulating surfaces.

The alumina was made by sintering Ceralox APA-0.5 MgO alumina at about 1400 C. for about 60 minutes and then hipping at 1350 C. and 200 MPa for 45 minutes. The resulting ceramic had a density of at least 3.97 g/cc; and a grain size of between 0.4 and 0.9 um (by linear intercept method), and a 4 point flexural strength of at least 550 MPa.

The YTZP zirconia was made by mixing a rare earth oxide powder and submicron zirconia powder, cold isostatically pressing the mixture at between 50 and 400 MPa, appropriately green machining the body to form a green sphere, sintering at between about 1300° C. and 1500° C. for about 1 to 4 hours to achieve a density of at least 95%; and hipping the sintered piece in an inert gas at between 1300° C. and 1500° C. for between 0.5 and 4 hours. The resulting ceramic had a density of at least 99.9%, a grain size of between 0.3 and 0.8 um, and a four point flexural strength of at least about 920 MPa.

These materials were tested by the pin-on-disk method, wherein a pin with a hemispherical tip was slid on the flat surface of a rotating disk, thus describing a circular unidirectional path. Four combination were tested: zirconia pin-zirconia disk, zirconia pin-alumina disk, alumina pin-alumina disk, and alumina pin-zirconia disk. Each disk had a surface roughness Ra of about 12.7 nm (0.5 uin). The zirconia pins had a roughness of about 25.4 nm (1 uin), while the alumina pins had a surface roughness of about 51–102 nm (2–4 uin).

The tests were performed on an ISC-200 PC tribometer (available from Implant Sciences Corp., Wakefield, Mass. 01880) using pins with a 12.7 mm (half inch) diameter hemispherical tip and disks 5.08 cm (2.0 inch) in diameter by 0.635 cm (0.25 inch) thick. The tests were run at room temperature, lubricated with bovine calf serum containing a bactericide and a precipitation inhibitor and at a sliding speed of 5 cm/sec. The travel distance of the pin on the disk was typically 350 meters. The applied load on the pin was 4.903N (500 gf), corresponding to an initial average contact Hertzian stress of 460 MPa for the zirconia-zirconia pair, 510 MPa for the mixed pairs, and 580 MPa for the alumina pair. The initial contact diameter was calculated to be approximately 0.1 mm for all the pairs. Each pair was run at least three times using the same pin and disk in different locations.

After 350 m, no wear could be detected on the disks by profilometry. The wear tracks on the disks were not visible to the naked eye except for the zirconia-zirconia pair, and then only faintly. In contrast, the wear on the pins was readily observable, as they exhibited the typical round to elliptical wear scars. There was no evidence of microcracking or brittle fracture in the wear areas, as examined by SEM.

The values reported in Table IV below for each pair represent the average of the wear factors values obtained in each run. Good reproducibility was obtained for each run.

TABLE IV

| Run | Pin | Disk | Wear Factor k | Friction Coeff't |
|---|---|---|---|---|
| 1 | Zirconia | Alumina | $1.6 \times 10^{-8}$ | 0.079 |
| 2 | Alumina | Zirconia | $1.6 \times 10^{-8}$ | 0.119 |
| 3 | Alumina | Alumina | $1.8 \times 10^{-8}$ | 0.134 |
| 4 | Zirconia | Zirconia | $2.2 \times 10^{-7}$ | 0.186 |

This example shows that the mixed pairs have superior wear factors over the even the alumina-alumina pair, and that the zirconia pin-alumina disk combination has the lowest coefficient of friction.

EXAMPLE V

These two experiments were performed in a manner substantially similarly to Example I, except that each substrate was subjected to a heat treatment of only two hours. In experiment A, the ball had a surface roughness Ra of about 10 nm and the plate had a surface roughness of about 10 nm. In Experiment B, the ball had a surface roughness Ra of about 10 nm and the plate had a surface roughness of about 100 nm. Simply, the plate of Experiment B was only machined and therefore was rougher than its counterpart in Experiment A. The combinations were test under a load of 10N.

The results of the test are shown in Table VI below:

TABLE VI

| Experiment | Ball Ra (nm) | Plate Ra (nm) | Wear Factor k |
|---|---|---|---|
| A | 10 | 10 | $5 \times 10^{-8}$ |
| B | 10 | 100 | $2 \times 10^{-6}$ |

These results are further evidence that each counterface must have a fine surface finish in order to produce wear factors considered desirable for articulating surfaces in a hip joint prosthesis.

For the purposes of the present invention, surface roughness Ra is determined via contact profilometry with a 2 um radius diamond stylus and a cutoff length of 0.08 mm.

We claim:

1. A joint prosthesis comprising:
   a) a prosthetic comprising a monolithic YTZP first component having an outer surface comprising at least 90 mol % zirconia, and
   b) a second component having a surface shaped to receive the outer surface of the first component,
   wherein the outer surface of the first component is received on the surface of the second component, and
   wherein a) at least a portion of the surface of the second component receiving the first component comprises a ceramic having a surface roughness of no more than 100 nm, and b) the outer surface of the monolithic YTZP first component has a surface roughness of no more than 100 nm.

2. The prosthesis of claim 1 wherein the joint is a hip joint, the first component is a substantially spherical ceramic head, the second component is an acetabular cup having a socket surface shaped to rotatably receive the outer surface of the ceramic head, wherein the outer surface of the ceramic head is received in the socket surface of the acetabular cup, and wherein a) at least a portion of the socket surface receiving the head comprises a ceramic having a surface roughness of no more than 50 nm, and b) the outer surface of the head has a surface roughness of no more than 50 nm.

3. The prosthesis of claim 2 wherein the portion of the socket surface comprising a ceramic comprises at least one oxide.

4. The prosthesis of claim 3 wherein the portion of the socket surface comprising a ceramic comprises at least about 50% alumina.

5. The prosthesis of claim 3 wherein the ceramic comprising at least one oxide is selected from the group consisting of a ceramic consisting essentially of alumina having a grain size of less than one micron, YTZP zirconia having a surface roughness of no more than 15 nm, and zirconia-toughened alumina.

6. The prosthesis of claim 1 wherein the ceramic comprising at least one oxide is a ceramic consisting essentially of alumina.

7. The prosthesis of claim 6 wherein the head has a surface roughness Ra of no more than 10 nm.

8. The prosthesis of claim 2 wherein the outer surface of the ceramic head and the socket surface each have a surface roughness Ra of no more than 15 nm.

9. The prosthesis of claim 2 wherein the outer surface of the head has a monoclinic zirconia content of less than 10%.

10. The prosthesis of claim 6 wherein the outer surface of the head and the ceramic socket surface each have a surface roughness Ra of no more than 15 nm.

11. The prosthesis of claim 2 wherein the socket surface consists essentially of alumina, and wherein the surface roughness Ra of the outer surface of the head is at least twice the surface roughness Ra of the socket surface.

12. The prosthesis of claim 6 wherein the outer surface of the head and the ceramic socket surface each have a surface roughness Ra of no more than 10 nm.

13. The prosthesis of claim 1 wherein the articulating surfaces of the first and second components are selected such that each has a wear factor of less than $10^{-7}$ mm$^3$/Nm when subjected in tandem to ASTM G99 wherein the pin is the material of the outer surface of the first component and the plate is the material of the surface of the second component.

14. The prosthesis of claim 2 wherein the outer surface of the ceramic head and the socket surface of the acetabular cup are selected such that each has a wear factor of less than $10^{-7}$ mm$^3$/Nm when subjected in tandem to ASTM G99 wherein the pin is the material of the outer surface of the ceramic head and the plate is the material of the socket surface of the acetabular cup.

15. The prosthesis of claim 10 wherein the outer surface of the ceramic head and the socket surface of the acetabular cup are selected such that each has a wear factor of less than $10^{-7}$ mm$^3$/Nm when subjected in tandem to ASTM G99 wherein the pin is the material of the outer surface of the ceramic head and the plate is the material of the socket surface of the acetabular cup.

16. The prosthesis of claim 1 wherein at least a portion of the surface of the second component receiving the first component comprises a ceramic has a surface roughness of no more than 50 nm.

17. The prosthesis of claim 16 wherein the outer surface of the first component has a surface roughness of no more than 50 nm.

18. The prosthesis of claim 1 wherein the joint is a hip joint, the first component is a head and the second component is a cup.

19. The prosthesis of claim 18 wherein the socket surface consists essentially of YTZP.

20. The prosthesis of claim 19 wherein the socket surface and the outer surface of the head each have a surface roughness Ra of no more than 15 nm.

21. The prosthesis of claim 19 wherein the socket surface and the outer surface of the head each have a surface roughness Ra of no more than 10 nm.

22. The prosthesis of claim 19 wherein the socket surface and the outer surface of the head each have a surface roughness Ra of no more than 5 nm.

23. The prosthesis of claim 18 wherein the socket surface is zirconia-toughened alumina.

24. The prosthesis of claim 23 wherein the socket surface and the outer surface of the head each have a surface roughness Ra of no more than 20 nm.

25. The prosthesis of claim 23 wherein the socket surface and the outer surface of the head each have a surface roughness Ra of no more than 10 nm.

26. The prosthesis of claim 23 wherein the socket surface and the outer surface of the head each have a surface roughness Ra of no more than 5 nm.

27. The prosthesis of claim 18 wherein the zirconia-toughened alumina comprises at least 20 mol % zirconia.

28. The prosthesis of claim 27 wherein the socket surface and the outer surface of the head each have a surface roughness Ra of no more than 20 nm.

29. The prosthesis of claim 27 wherein the socket surface and the outer surface of the head each have a surface roughness Ra of no more than 10 nm.

30. The prosthesis of claim 27 wherein the socket surface and the outer surface of the head each have a surface roughness Ra of no more than 5 nm.

31. The prosthesis of claim 1 wherein the joint is a hip joint, the second component is a substantially spherical ceramic head consisting essentially of alumina, the first component is an acetabular cup having a monolithic YTZP socket surface shaped to rotatably receive the outer surface of the ceramic head, wherein the outer surface of the ceramic head is received in the socket surface of the acetabular cup, and wherein a) at least a portion of the socket surface receiving the head comprises a ceramic having a surface roughness of no more than 50 nm, and b) the outer surface of the head has a surface roughness of no more than 50 nm.

32. The prosthesis of claim 31 wherein the socket surface and the outer surface of the head each have a surface roughness Ra of no more than 20 nm.

33. An acetabular cup having a monolithic socket for receiving a ceramic femoral head having a surface roughness Ra of no more than 50 nm, wherein the improvement comprises the monolithic socket consists essentially of YTZP and has a surface roughness of no more than 50 nm.

34. A knee joint prosthesis comprising:

a) a femoral component having a base and a plurality of tynes extending therefrom in the same direction, and b) a tibial plate having a surface shaped for receiving the tynes, wherein the tynes have an outer surface comprising zirconia partially stabilized by between 2 mol % and 5 mol % rare earth oxide and a surface roughness of no more than 100 nm, and wherein the surface of the tibial plate receiving the tynes is a ceramic having a surface roughness of no more than 100 nm.

35. The knee joint prosthesis of claim 34 wherein the outer surface of the tynes have a surface roughness of no more than 50 nm.

36. The knee joint of claim 35 wherein the surface of the tibial plate receiving the tynes has a surface roughness of no more than 50 nm.

* * * * *